United States Patent [19]

Petzoldt et al.

[11] 4,307,088
[45] Dec. 22, 1981

[54] 1-HYDROXY STEROIDS, A PROCESS FOR THE PRODUCTION THEREOF, AND PHARMACEUTICAL PREPARATIONS CONTAINING THEM

[75] Inventors: Karl Petzoldt; Rudolf Wiechert; Hermann Steinbeck; Walter Elger, all of Berlin, Fed. Rep. of Germany

[73] Assignee: Schering Aktiengesellschaft, Berlin and Bergkamen, Fed. Rep. of Germany

[21] Appl. No.: 227,304

[22] Filed: Jan. 22, 1981

[30] Foreign Application Priority Data

Jan. 23, 1980 [DE] Fed. Rep. of Germany ....... 3002746

[51] Int. Cl.³ .......................... A61K 31/56; C07J 7/00
[52] U.S. Cl. ................................ 424/243; 260/397.4; 435/52
[58] Field of Search ........................................ 424/243

[56] References Cited

U.S. PATENT DOCUMENTS 3,981,894  9/1976  Phillipps et al. ................. 260/397.1
4,124,708  11/1978  Elger et al. .......................... 424/243
4,144,334  3/1979  Petzold et al. ................... 260/397.4

Primary Examiner—Elbert L. Roberts
Attorney, Agent, or Firm—Millen & White

[57] ABSTRACT

1-Hydroxy steroids of formula I

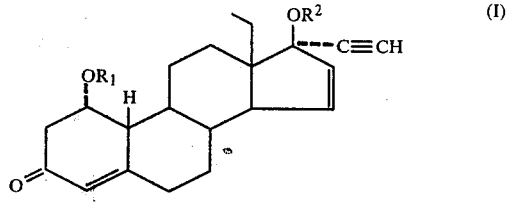

wherein
$R_1$ and $R_2$ are independently hydrogen or alkanoyl of 1–8 carbon atoms are distinguished by strong progestational activity and only very minor androgenic side effects.

8 Claims, No Drawings

1-HYDROXY STEROIDS, A PROCESS FOR THE PRODUCTION THEREOF, AND PHARMACEUTICAL PREPARATIONS CONTAINING THEM

The present invention relates to 1-hydroxy steroids, a process for the production thereof, and pharmaceutical preparations containing them.

SUMMARY OF THE INVENTION

It is an object of this invention to provide new steroidal compounds having valuable pharmacological properties.

Upon further study of the specification and appended claims, further objects and advantages of this invention will become apparent to those skilled in the art.

These objects have been attained by providing compounds of Formula I

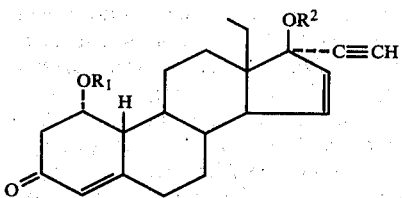

wherein
$R_1$ and $R_2$ are independently hydrogen or alkanoyl of 1-8 carbon atoms.

DETAILED DISCUSSION

In Formula I, the groups $R_1$ and $R_2$ can be identical or different and are hydrogen or alkanoyl of 1-8 carbon atoms. Examples include formyl, acetyl, propionyl, butyryl, pentanoyl, hexanoyl, heptanoyl and octanoyl. Preferred as $R_1$ is acetyl or especially hydrogen. Preferred as $R_2$ is hydrogen.

The novel 1-hydroxy steroids of this invention can be produced by fermenting a compound of Formula II

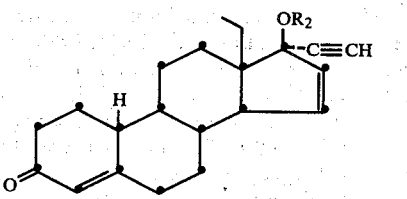

Wherein $R_2$ is as defined above, with a fungal culture of the genus Aspergillus, Calonectria, Mucor, Glomerella, or Septomyxa, and, optionally, esterifying free hydroxy groups.

This process can be conducted, for example, using the following fungal strains:

| | |
|---|---|
| *Aspergillus clavatus* | (ATCC 9598) |
| *Calonectria decora* | (ATCC 14767) |
| *Mucor griseocyanus* | (ATCC 1207 b) |
| *Glomerella glycines* | (ATCC 11871) |
| *Septomyxa affinis* | (ATCC 6737) |

The strain *Aspergillus clavatus* is preferably used.

The hydroxylation can be conducted according to methods customarily employed for the microbiological hydroxylation of steroids with fungal cultures. Appropriate conditions can be selected fully conventionally. See, e.g., A. Capec et al., Microbial Transformation of Steroids, pages 65–68 especially, whose disclosure is incorporated by reference herein.

Thus, first of all, the most favorable fermentation conditions can be determined by the generally customary preliminary tests, such as, for example, the selection of the most advantageous nutrient medium, the suitable substrate solvent, the substrate concentration, the technical conditions, such as temperature, aeration, pH, and the optimum times for germination, substrate addition, and substrate contact of the microorganism on the enzyme; this can be accomplished analytically, especially by thin-layer chromatography.

In this connection, it has been found that it is advantageous to utilize concentrations of about 50–1000 mg of substrate per liter of nutrient medium. The pH value is preferably adjusted to a value in the range of 5 to 7. The incubation temperature is 20° to 40° C., preferably 25° to 35° C. For aeration, about 1 liter of air is introduced per minute per liter of culture broth. The conversion of the substrate is suitably controlled by analysis of sample extracts by means of thin-layer chromatography. In general, sufficient amounts of hydroxylated steroids have been formed after 20–120 hours.

After fermentation is completed, the fermentation products are conventionally isolated. The isolation can be effected, for example, by extracting the fermentation batches with a polar, water-insoluble solvent, such as ethyl acetate, butyl acetate, or methyl isobutyl ketone; concentrating the extracts by evaporation; and purifying the thus-obtained crude products, if desired, by chromatography and/or crystallization.

The optional esterification of the free hydroxy groups can also be effected using methods customarily employed in steroid chemistry for esterification of secondary and tertiary hydroxy groups. A suitable esterification method, for example, is the reaction of the steroids with acid anhydrides or acid chlorides in the presence of alkaline catalysts, such as sodium bicarbonate, potassium bicarbonate, potassium carbonate, sodium hydroxide, potassium hydroxide, pyridine, lutidine, collidine, or 4-dimethylaminopyridine. Depending on the conventional choice of reaction conditions and reaction periods, the products are the 1-mono- or 1,17-diacyl steroids. Thus, at reaction temperatures of 0°–30° C., the monoacyl steroids are primarily obtained within 10–20 hours, and at reaction temperatures of 10°–50° C., the diacyl steroids are the predominant reaction products within 20–100 hours. A partial esterification of the 17-hydroxy group is not possible. A mixture of the 1-hydroxy-17-monoacyl and the 1,17-dihydroxy steroids is obtained if the microbiological hydroxylation is conducted with the 17-acyl compound of Formula II.

The novel 1-hydroxy steroids of this invention are pharmacologically active compounds suitable for administration to mammals, including humans. They exhibit a spectrum of effectiveness similar to that of steroids which are not hydroxylated in the 1-position. Thus, the compounds of Formula I are distinguished by a strong progestational effect. For example, 17α-ethynyl-1α,17-dihydroxy-18-methyl-4,15-estradien-3-one (A) has been proven to be superior to the non-hydroxylated 17α-ethynyl-17-hydroxy-18-methyl-4,15-estradien-3-one (B) in the conventional Clauberg test.

The following table gives the McPhail values obtained after conventional oral administration of these compounds to infantile female rabbits.

| | Clauberg Test p.o. | |
|---|---|---|
| Compound | Dose (mg) | McPhail |
| A | 0.03 | 3.1 |
| | 0.01 | 1.9 |
| B | 0.03 | 2.9 |
| | 0.01 | 1.6 |

Determination was made in accordance with the McPhail scale. (Evaluating grades 1-4 wherein 1=no transformation of endometrium, 4=complete transformation of endometrium.)

Moreover, the novel 1-hydroxy steroids of this invention show only a very minor androgenic side effect.

The higher esters (e.g., —8 carbon atoms) of the compounds of this invention are distinguished by prolonged activity.

The compounds of this invention can be utilized, for example, in contraceptive preparations as the progestational component in combination with an estrogenically active hormonal component, e.g., ethynylestradiol, or as the sole active component. The compounds can also be employed, however, in preparations for the treatment of the usual gynecological disorders, e.g., cycle irregularities in case of inadequate function of the corups luteum, climacteric complaints, depressive mood, etc.

For medicinal use, the novel compounds can be processed into the conventional forms of medicines using the additives, vehicles, and flavor-ameliorating agents which are customary in galenic pharmacy according to methods known per se. Especially suitable for oral administration are tablets, dragees, capsules, pills, suspensions, or solutions. Particularly suitable for parenteral administration are oily solutions, e.g., sesame oil or castor oil solutions, which can optionally contain additionally a diluent, such as, for example, benzyl benzoate or benzyl alcohol.

The concentration of the active agent is dependent on the form of administration. Thus, tablets for oral administration, for example, contain preferably 0.01-0.5 mg of active compound, and solutions for parenteral administration contain preferably 1-100 mg of active compound per 1 ml of solution.

The dosages of the medicines according to this invention vary conventionally with the type and purpose of administration. For example, the daily contraceptive dose upon oral administration is 0.01-0.5 mg. Administration is fully analogous to that of the conventional agent norgestrel (U.S. Pat. No. 3,959,322) or lynestrenol (U.S. Pat. No. 2,966,503). Dosages for a given host and a given indication can be determined, e.g., by customary comparison of the activities of the subject compound and of a known agent by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A 2-liter Erlenmeyer flask containing 500 ml of a nutrient solution sterilized in an autoclave for 30 minutes at 120° C. and consisting of 3.0% glucose, 1.0% corn steep liquor, 0.2% $NaNO_3$, 0.1% $KH_2PO_4$, 0.2% $K_2HPO_4$, 0.05% $MgSO_4.7H_2O$, 0.002% $FeSO_4.7H_2O$, and 0.05% KCl, is inoculated with a slanted-tube culture of the strain *Aspergillus clavatus* (ATCC 9598) and shaken for 2½ days on a rotary shaker. Then, a 20-liter preliminary fermentor is inoculated with 250 ml of this germination culture, this fermentor having been filled with 15 l of a medium having the same composition as the germination culture and sterilized for 60 minutes at 121° C. and 1.1 atmosphere gauge. When the addition of "Silicon SH" as the defrother, the mixture is germinated for 24 hours at 29° C. and under 0.7 atmosphere gauge pressure under aeration (10 l/min) and agitation (220 rpm). Thereafter, 900 ml of this culture is withdrawn under sterile conditions and a 20-liter main fermentor is inoculated therewith, which is charged with 14 l of a nutrient medium having the same composition as the preliminary fermentor culture and having been sterilized as set forth above. After a culture period of 12 hours under preliminary fermentor conditions, 3 g of 17α-ethynyl-17-hydroxy-18-methyl-4,15-estradien-3-one, dissolved in 150 ml of dimethylformamide, is added under sterile conditions, and agitation and aeration are continued. The course of the fermentation is controlled by the withdrawal of samples which are extracted with methyl isobutyl ketone and analyzed by thin-layer chromatography. After a contact period of 92 hours, the conversion of the substrate is terminated. The content of the fermentor is extracted twice with respectively 10 l of methyl isobutyl ketone, the extracts are combined and initially concentrated in a forced-circulation evaporator and then concentrated to dryness at a bath temperature of 50° C. under vacuum in a rotary evaporator. The residue is dissolved in warm methanol, filtered off from the silicone oil which has remained undissolved, again evaporated to dryness, and chromatographed over a silica gel column (gradient elution:-hexane-hexane/ethyl acetate 1:1). Therefter the product is dissolved under boiling in a small amount of benzene and gradually cooled down, thus crystallizing the 1α-hydroxy compound as a pure, crystalline solvate (1.56 g), mp 129°–130° C., with 0.5 mole of benzene. To separate the benzene-solvate, the substance is dissolved in a small amount of ethanol, combined with distilled water until the onset of turbidity, and the benzene is distilled off azeotropically under vacuum. Subsequently, the clear solution is freeze-dried, thus obtaining the 17α-ethynyl-1α,17-dihydroxy-18-methyl-4,15-estradien-3-one in the form of a powdery-amorphous, very easily administrable product.

EXAMPLE 2

200 mg of 17α-ethynyl-1α,17-dihydroxy-18-methyl-4,15-estradien-3-one is dissolved in 10 ml of pyridine and combined under ice-cooling dropwise with 3 m of acetic anhydride. The solution is then allowed to warm up and agitated at room temperature overnight. Thereafter the reaction mixture is stirred into ice water, the precipitated, oily-crystalline product is vacuum-filtered, taken up in ethyl acetate, washed neutral, dried over $Na_2SO_4$, and concentrated to dryness under vacuum. The remaining residue is crystallized from ether/hexane, thus obtaining 165 mg of 1α-acetoxy-17α-ethynyl-17-hydroxy-18-methyl-4,15-estradien-3-one, mp 123°–126° C.

EXAMPLE 3

Under the conditions of Example 2, 200 mg of 17α-ethynyl-1α,17-dihydroxy-18-methyl-4,15-estradien-3-one is reacted with butyric anhydride, thus obtaining 140 mg of 17α-ethynyl-1α-butyryloxy-17-hydroxy-18-methyl-4,15-estradien-3-one of oily consistency.

EXAMPLE 4

Under the conditions of Example 2, 200 mg of 17α-ethynyl-1α,17-dihydroxy-18-methyl-4,15-estradien-3-one is reacted with caprylic anhydride, thus obtaining 130 mg of 17α-ethynyl-17-hydroxy-18-methyl-1α-octanoyloxy-4,15-estradien-3-one of an oily consistency.

EXAMPLE 5

200 mg of 17α-ethynyl-1α,17-dihydroxy-18-methyl-4,15-estradien-3-one is combined with 10 ml of pyridine and 3 ml of acetic anhydride and stirred for 4 days at room temperature under nitrogen. Thereafter the reaction mixture is evaporated under a high vacuum, the residue is taken up in ethyl acetate and washed neutral with distilled water. After drying over sodium sulfate and concentration of the ethyl acetate solution under vacuum, 17α-ethynyl-1α,17-diacetoxy-18-methyl-4,15-estradien-3-one is obtained as an oil.

EXAMPLE 6

(Composition of a Tablet)

| | |
|---|---|
| 0.075 mg | 17α-Ethynyl-1α,17-dihydroxy-18-methyl-4,15-estradien-3-one |
| 0.030 mg | 17α-Ethynylestradiol |
| 109.895 mg | Lactose (DAB 6) |
| 8.000 mg | Corn starch (USP XVI) |
| 1.000 mg | Magnesium stearate (USP XVI) |
| 1.000 mg | Talc |
| 120.000 mg | Total weight of Tablet |

EXAMPLE 7

(Composition of a Dragee)

| | |
|---|---|
| 0.100 mg | 17α-Ethynyl-1α,17-dihydroxy-18-methyl-4,15-estradien-3-one |
| 0.020 mg | 17α-Ethynylestradiol |
| 31.880 mg | Lactose |
| 18.425 mg | Corn starch |
| 2.060 mg | polyvinylpyrrolidone 25 |
| 0.010 mg | Methylparaben |
| 0.005 mg | Propylparaben |
| 2.500 mg | Talc |
| 55.000 mg | Total weight of Tablet, made into a dragee of |

| | |
|---|---|
| about 90 mg with the usual sugar mixture | |

EXAMPLE 8

(Composition of a Tablet)

| | |
|---|---|
| 0.100 mg | 17α-Ethynyl-1α,17-dihydroxy-18-methyl-4,15-estradien-3-one |
| 63.600 mg | Lactose |
| 15.000 mg | Microcrystalline cellulose |
| 1.000 mg | Talc |
| 0.300 mg | Magnesium stearate |
| 80.000 mg | Total weight of Tablet |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1-hydroxy steroid of the formula

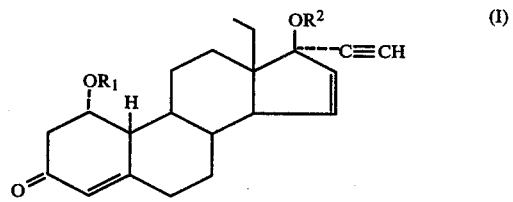

wherein $R_1$ and $R_2$ each independently is hydrogen or alkanoyl of 1–8 carbon atoms.

2. 17α-Ethynyl-1α,17-dihydroxy-18-methyl-4,15-estradien-3-one, a compound of claim 1.

3. 1α-Acetoxy-17α-ethynyl-17-hydroxy-18-methyl-4,15-estradien-3-one, a compound of claim 1.

4. 17α-Ethynyl-1α-butyryloxy-17-hydroxy-18-methyl-4,15-estradien-3-one, a compound of claim 1.

5. 17α-Ethynyl-17-hydroxy-18-methyl-1α-octanoyloxy-4,15-estradien-3-one, a compound of claim 1.

6. 17α-Ethynyl-1α,17-diacetoxy-18-methyl-4,15-estradien-3-one, a compound of claim 1.

7. A pharmaceutical composition comprising a progestationally effective amount of a compound of claim 1 and a pharmaceutically acceptable carrier.

8. A method of achieving birth control in a host in need of the same comprising administering a progestationally effective amount of a compound of claim 1 to the host.

* * * * *